(12) United States Patent
Otsuka et al.

(10) Patent No.: US 10,527,498 B2
(45) Date of Patent: Jan. 7, 2020

(54) SENSOR DEVICE

(71) Applicant: DENSO CORPORATION, Kariya, Aichi-pref. (JP)

(72) Inventors: Kiyoshi Otsuka, Kariya (JP); Junichi Ishikawa, Kariya (JP); Hirotaka Kurozaki, Kariya (JP)

(73) Assignee: DENSO CORPORATION, Kariya (JP)

( * ) Notice: Subject to any disclaimer, the term of this patent is extended or adjusted under 35 U.S.C. 154(b) by 318 days.

(21) Appl. No.: 15/559,109

(22) PCT Filed: May 24, 2016

(86) PCT No.: PCT/JP2016/002511
§ 371 (c)(1),
(2) Date: Sep. 18, 2017

(87) PCT Pub. No.: WO2016/194334
PCT Pub. Date: Dec. 8, 2016

(65) Prior Publication Data
US 2018/0156670 A1 Jun. 7, 2018

(30) Foreign Application Priority Data

Jun. 1, 2015 (JP) .................................. 2015-111728
May 7, 2016 (JP) .................................. 2016-093519

(51) Int. Cl.
G01K 1/14 (2006.01)
G01N 27/02 (2006.01)
(Continued)

(52) U.S. Cl.
CPC .............. *G01K 1/143* (2013.01); *G01K 7/16* (2013.01); *G01N 27/02* (2013.01); *H05K 1/0201* (2013.01);
(Continued)

(58) Field of Classification Search
CPC ............. G01K 1/14; G01K 1/16; G01K 1/143
(Continued)

(56) References Cited

U.S. PATENT DOCUMENTS 5,618,109 A * 4/1997 Culbertson .............. G01K 7/04
136/201
7,441,950 B2 * 10/2008 Kamiyama .............. G01K 7/42
338/28

(Continued)

FOREIGN PATENT DOCUMENTS

DE 10 2006 060 548 A1 6/2008
JP S62-055157 U 4/1987
(Continued)

*Primary Examiner* — Gail Kaplan Verbitsky
(74) *Attorney, Agent, or Firm* — Posz Law Group, PLC

(57) ABSTRACT

A sensor device includes a sensor element detecting a temperature of an attachment member to which the sensor device is attached. The sensor device includes a flexible substrate that includes a base having a first surface and a second surface and made of an electrically insulating material, and a land disposed adjacent to the first surface and electrically connected to the sensor element. The sensor device further includes: a rigid member adhered to the second surface; a flexible member that has a thermal conductivity and a flexibility higher than those of the base, is stacked on the rigid member to be in contact with the rigid member on a side opposite to the flexible substrate, and is to be in contact with the attachment member in an attached state; and a pressing member that presses the flexible substrate toward the attachment member in the attached state.

13 Claims, 6 Drawing Sheets

(51) Int. Cl.
  *G01K 7/16* (2006.01)
  *H05K 1/02* (2006.01)
  *H05K 1/11* (2006.01)
  *H05K 1/18* (2006.01)
  *G01V 8/12* (2006.01)

(52) U.S. Cl.
  CPC ............ *H05K 1/028* (2013.01); *H05K 1/116* (2013.01); *H05K 1/18* (2013.01); *G01V 8/12* (2013.01); *H05K 2201/10151* (2013.01)

(58) Field of Classification Search
  USPC ........................................................ 374/208
  See application file for complete search history.

(56) References Cited

U.S. PATENT DOCUMENTS

| | | | | |
|---|---|---|---|---|
| 8,083,402 | B2* | 12/2011 | Mau | G01J 5/04 |
| | | | | 374/109 |
| 8,496,377 | B2* | 7/2013 | Harr | G01K 1/14 |
| | | | | 374/163 |
| 10,113,915 | B1* | 10/2018 | Bhat | G01J 5/12 |
| 2008/0016945 | A1 | 1/2008 | Rothacher et al. | |

FOREIGN PATENT DOCUMENTS

| | | |
|---|---|---|
| JP | H08-068699 A | 3/1996 |
| JP | 2001-091363 A | 4/2001 |
| JP | 2003-337112 A | 11/2003 |
| JP | 3184781 U | 6/2013 |
| JP | 2014-038056 A | 2/2014 |
| JP | 2015-030430 A | 2/2015 |

\* cited by examiner

SENSOR DEVICE

CROSS REFERENCE TO RELATED APPLICATIONS

This application is a U.S. national stage of International Patent Application No. PCT/JP2016/002511 filed on May 24, 2016 and is based on Japanese Patent Applications No. 2015-111728 filed on Jun. 1, 2015 and No. 2016-93519 filed on May 7, 2016, the disclosures of which are incorporated herein by reference.

TECHNICAL FIELD

The present disclosure relates to a sensor device that has a sensor element, and detects, in an attached state of being attached to an attachment member, the temperature of the attachment member through the sensor element.

BACKGROUND ART

Conventionally, an integrated sensor apparatus (sensor device) attached to a windshield (attachment member) has been known, as described in Patent Literature 1. The integrated sensor apparatus includes a vehicle interior temperature detecting element (sensor element), a first substrate, a contact member (flexible member), and a housing (pressing member). The vehicle interior temperature detecting element is mounted on the first substrate on a side opposite to the windshield. The contact member is disposed between the first substrate and the windshield. The housing is connected to the first substrate and the windshield, and presses the first substrate against the windshield.

The contact member is closely in contact with the first substrate and the windshield, so heat conduction is enabled from the windshield to the vehicle interior temperature detecting element through the first substrate. In other words, the heat conduction from the windshield to the vehicle interior temperature detecting element can be ensured by the contact member.

PRIOR ART LITERATURE

Patent Literature

Patent Literature 1: JP 2015-30430 A

SUMMARY OF INVENTION

For example, in order to improve flexibility in arrangement, it is concerned to use a flexible substrate as the first substrate. In such a configuration, however, the flexible substrate easily deforms during an assembling step. Specifically, in the assembling step, a portion of the flexible substrate pressed by the housing is likely to be more deformed toward the windshield than a portion of the flexible substrate that is not pressed by the housing. If the flexible substrate is deformed, a reliability in electric connection between the vehicle interior temperature detecting element and the flexible substrate is likely to be deteriorated.

It is an object of the present disclosure to provide a sensor device that is capable of suppressing deterioration of the reliability in electric connection between a flexible substrate and a sensor element while ensuring heat conduction from an attachment member to the sensor element.

According to an aspect of the present disclosure, a sensor device is to detect a temperature of an attachment member by a sensor element in an attached state of being attached to the attachment member. The sensor device includes: a sensor element that detects the temperature of the attachment member; a flexible substrate that includes a base having a first surface and a second surface opposite to the first surface and being made of an electrically insulating material, and a land being disposed adjacent to the first surface and being electrically connected to the sensor element; a rigid member that has a thermal conductivity and a rigidity higher than those of the base and is adhered to the second surface; a flexible member that has a thermal conductivity and a flexibility higher than those of the base, is in contact with and stacked on the rigid member on a side opposite to the flexible substrate, and is arranged to be in contact with the attachment member in the attached state; and a pressing member that presses the flexible substrate toward the attachment member in the attached state.

In the structure described above, the flexible member is closely in contact with the attachment member and the rigid member by being pressed by the pressing member. The rigid member is adhered to the flexible substrate. In these configurations, heat is easily conducted from the attachment member to the sensor element through the flexible member, the rigid member, and the flexible substrate. In other words, thermal conduction from the attachment member to the sensor element can be ensured.

In the structure described above, since the flexible substrate is adhered to the rigid member, the flexible substrate hardly deforms in an assembling step. Therefore, it is possible to suppress the degradation of the reliability in electric connection between the flexible substrate and the sensor element.

BRIEF DESCRIPTION OF DRAWINGS

The above and other objects, features and advantages of the present disclosure will become more apparent from the following detailed description made with reference to the accompanying drawings, in which.

DESCRIPTION OF EMBODIMENTS

Hereinafter, embodiments of the present disclosure will be described with reference to the drawings. In each of the embodiments described hereinafter, components that are in common or relevant to each other will be designated with the same reference numbers. A stacking direction will be indicated as a Z direction, a specific direction orthogonal to the Z direction will be indicated as an X direction, and a direction orthogonal to both of the Z direction and the X direction will be indicated as a Y direction. A plane including the X direction and the Y direction will be indicated as an XY plane. Also, a shape along the XY plane will be indicated as a planar shape, if there is no special explanation.

(First Embodiment)

Firstly, a schematic structure of a sensor device 10 will be described with reference to FIG. 1 and FIG. 2.

Figure 1:
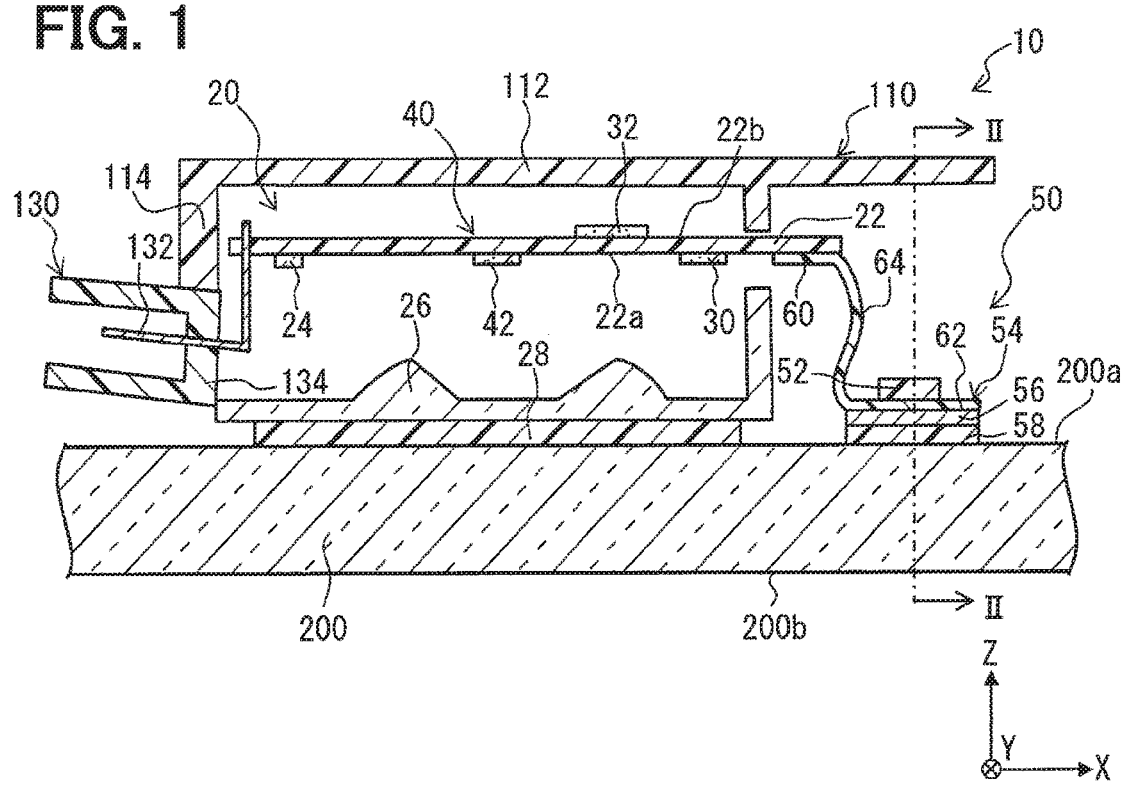
FIG. 1 is a cross-sectional view for illustrating a schematic structure of a sensor device according to a first embodiment.

As shown in FIG. 1, the sensor device 10 is a device that is attached to an attachment member 200 to detect the temperature of the attachment member 200. In the present embodiment, the attachment member 200 is a windshield of a vehicle. The attachment member 200 has a surface 200a, and a rear surface 200b opposite to the surface 200a. The surface 200a is an interior surface of the attachment member 200 facing a compartment of the vehicle. The sensor device 10 is arranged on the surface 200a.

In the present embodiment, the sensor device 10 includes a rain detection unit 20, a light detection unit 40, a temperature-humidity detection unit 50, a housing 110, and a connector 130. Hereinafter, a schematic structure of the sensor device 10 in an attached state where the sensor device 10 is attached to the attachment member 200 will be described.

The rain detection unit 20 includes a printed board 22, an LED 24, a lens 26, a sheet 28, a PD 30, and an arithmetic unit 32. The printed board 22 has a surface 22a adjacent to the attachment member 200, and a rear surface 22b opposite to the surface 22a. The LED 24 and the PD 30 are mounted on the surface 22a. The arithmetic unit 32 is mounted on the rear surface 22b. Note that the arithmetic unit 32 may be mounted on the surface 22a, in place of the rear surface 22b. The LED 24, the PD 30, the arithmetic unit 32 correspond to electronic components.

The LED 24 emits light toward the attachment member 200. The light emitted from the LED 24 enters the lens 26. The lens 26 is a member that guides the light of the LED 24. A sheet 28 is disposed between the lens 26 and the attachment member 200. The sheet 28 is made of a material having high flexibility. The sheet 28 is in contact with the lens 26 and the attachment member 200. The sheet 28 is, for example, a silicone sheet.

The light of the LED 24 enters the attachment member 200 through the lens 26 and the sheet 28. In a state where raindrops are adhered on the rear surface 200b, the light of the LED 24 enters the raindrops without being reflected by the rear surface 200b. On the other hand, in a state where raindrops are not adhered on the rear surface 200b, the light of the LED 24 is reflected at the rear surface 200b. The light of the LED 24 reflected at the rear surface 200b enters the PD 30 through the sheet 28 and the lens 26. The lens 26 has an extending portion that extends toward the surface 22a so as to divide the rain detection unit 20 and the light detection unit 40 from the temperature-humidity detection unit 50.

The PD 30 receives the light of the LED 24, and outputs to the arithmetic unit 32 a detection signal according to an intensity of light received. The arithmetic unit 32 determines, based on the detection signal of the PD 30, presence or absence of raindrops adhering on the rear surface 200b, as well as the amount of the raindrops. The arithmetic unit 32 includes a control circuit, a communication circuit, and an arithmetic circuit, for example.

The light detection unit 40 detects an external light coming from outside of the vehicle. The light detection unit includes a PD 42, the printed board 22, and the arithmetic unit 32. The PD 42 is mounted on the surface 22a. The external light enters the PD 42 through the attachment member 200, the sheet 28 and the lens 26. The PD 42 receives the external light, and outputs to the arithmetic unit 32 a detection signal according to the intensity of light received. The arithmetic unit 32 determines, based on the detection signal of the PD 42, presence or absence of the external light, or the intensity of the external light. The PD 42 corresponds to an electronic component. Note that the PD 30 and the PD 42 will also be referred to as photo diodes or light receiving elements.

The temperature-humidity detection unit includes a temperature-humidity detecting element 52, a flexible substrate 54, a rigid member 56, a flexible member 58. The temperature-humidity detecting element 52 is an element that detects the temperature of the attachment member 200, and a humidity in the vicinity of the attachment member 200. In detail, the temperature-humidity detecting element 52 detects the temperature of the surface 200a, and the humidity in the vicinity of the surface 200a. The temperature-humidity detecting element 52 corresponds to a sensor element.

The temperature-humidity detecting element 52 outputs a detection signal according to the temperature and humidity detected to the arithmetic unit 32 through the flexible substrate 54 and the printed board 22. The arithmetic unit 32 calculates the temperature of the attachment member 200 and the humidity in the vicinity of the surface 200a based on the detection signal of the temperature-humidity detecting element 52. As another example, the arithmetic unit 32 may be configured to determine the presence or absence of raindrops adhering on the surface 200a based on the detection signal of the temperature-humidity detecting element 52.

The flexible substrate 54 includes a connection portion 60 connected to the printed board 22, a mounting portion 62 on which the temperature-humidity detecting element 52 is mounted, and an intervening portion 64 between the mounting portion 62 and the connection portion 60. The connection portion 60 is electrically connected to the printed board 22. The connection portion 60 is, for example, connected to the printed board 22 using a connector, solder and ACF. The printed board 22 has a rigidity higher than the flexible substrate 54.

Figure 2:
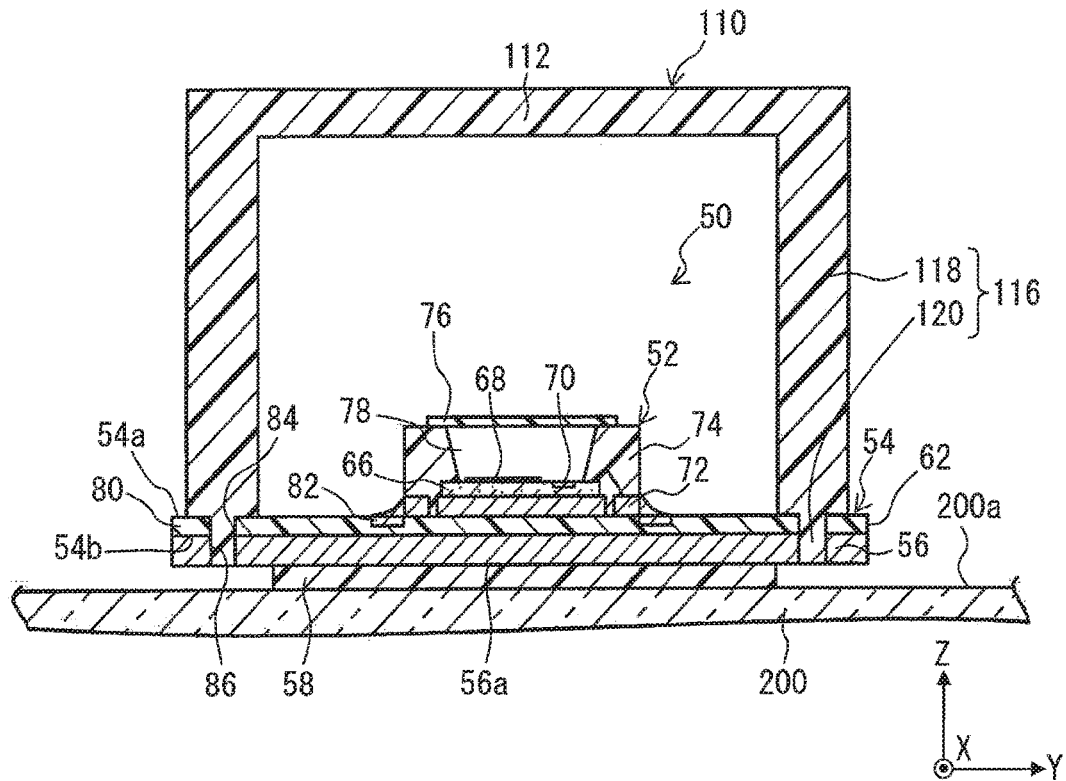
FIG. 2 is a cross-sectional view taken along a line II-II in FIG. 1.

As shown in FIG. 2, the flexible substrate 54 has a surface 54a, and a rear surface 54b opposite to the surface 54a. The surface 54a corresponds to a first surface. The rear surface 54b corresponds to a second surface. The mounting portion 62 has a flat plate shape having a thickness direction in the Z direction. The mounting portion 62, the rigid member 56 and the flexible member 58 are stacked in the Z direction. The structure of the temperature-humidity detection unit 50 will be described later in detail.

The housing 110 is a member that accommodates the rain detection unit 20 and the light detection unit 40 therein, and presses the temperature-humidity detection unit 50 against the attachment member 200. The housing 110 covers the rain detection unit 20, the light detection unit 40, and the temperature-humidity detection unit 50. The housing 110 at least accommodates the printed board 22 therein.

The housing 110 is fixed to the attachment member 200 through non-illustrated spring element and bracket. The bracket is adhered to the attachment member 200 and is engaged with the housing 110 through the spring element. As another example, the housing 110 may be fixed to the attachment member 200 only through an adhesive material.

The housing 110 has a flat plate portion 112, side wall portions 114, and a pressing portion 116. The flat plate portion 112 has a flat plate shape having a thickness in the Z direction. The flat plate portion 112 is disposed adjacent to the rear surface 22b of the printed board 22. The flat plate portion 112 is disposed to overlap with the rain detection unit 20, the light detection unit 40 and the temperature-humidity detection unit 50 in a projection view projected in the Z direction.

The side wall portions 114 extend from the ends of the flat plate portion 112 toward the attachment member 200, the ends including opposite ends of the flat plate portion 112 in the Y direction, and an end of the flat plate portion 112 in the X direction. Further, the side wall portions 114 extends from the flat plate portion 112 toward the rear surface 22b so as to separate the rain detection unit 20 and the light detection unit 40 from the temperature-humidity detection unit 50. Note that the temperature-humidity detection unit 50 is not tightly closed by the housing 110. Thus, the humidity around the temperature-humidity detection unit 50 can be made substantially same as the humidity of air outside of the sensor device 10. The structure of the pressing portion 116 will be described later in detail.

The connector 130 electrically relays between an external device and the arithmetic unit 32. The connector 130 is integrally molded with the housing 110, or attached to the housing 110. In the present embodiment, the connector 130 is attached to the housing 110.

The connector 130 includes a terminal 132 and a holding portion to hold the terminal 132. The holding portion 134 has a bottomed cylindrical shape having an opening at an end. The bottom of the holding portion 134 is engaged with the side wall portion 114 that extends from the one end of the flat plate portion 112 with respect to the X direction. The holding portion 134, the flat plate portion 112 and the side wall portions 114 form a space to accommodate the rain detection unit 20 and the light detection unit 40 therein.

The holding portion 134 engages with a connector of the external device. The terminal 132 has an end in a hollow space of the holding portion 134 to be connected to the external terminal. An opposite end of the terminal 132 is connected to the printed board 22. As described hereinabove, the arithmetic unit 32 can communicate with the external device through the terminal 132.

Figure 3:
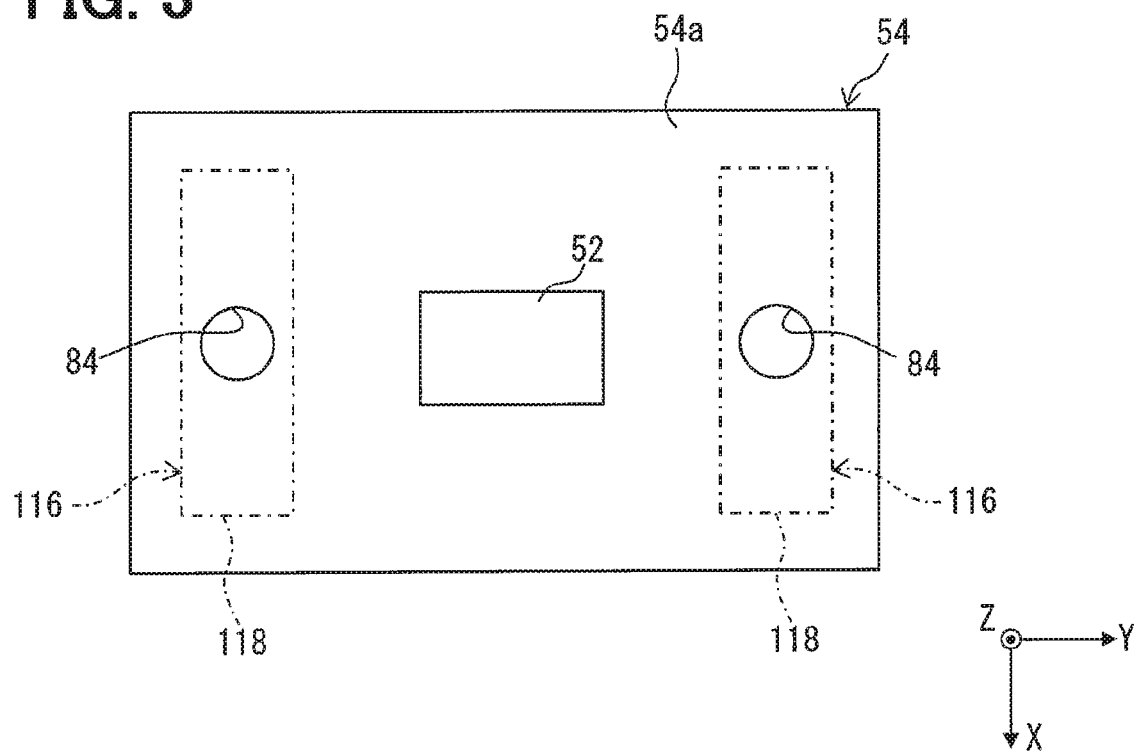
FIG. 3 is a plan view for illustrating a specific structure of a flexible substrate and a pressing portion.

Next, the specific structure of the temperature-humidity detection unit 50 will be described with reference to FIGS. 2 and 3.

As shown in FIG. 2, the temperature-humidity detecting element 52 includes a semiconductor substrate 66, a temperature detecting portion 68, a humidity detecting portion 70, a lead frame 72, a molded resin 74 and a moisture permeable filter 76. The semiconductor substrate 66 has a flat plate shape having a thickness in the Z direction. The temperature detecting portion 68 and the humidity detecting portion 70 are formed on the surface of the semiconductor substrate 66 opposite to the attachment member 200 in the Z direction.

The temperature detecting portion 68 is formed by treating the surface of the semiconductor substrate 66, for example, and has a resistance value that varies in accordance with a change of the temperature. The humidity detecting portion 70, for example, includes a moisture sensitive film and an electrode, and the moisture sensitive film has impedance that varies in accordance with a change of humidity. The semiconductor substrate 66 is arranged on the lead frame 72, and is electrically connected to the lead frame 72.

The surface of the semiconductor substrate 66 adjacent to the attachment member 200 is fixed to the lead frame 72. The lead frame 72 is electrically connected to the semiconductor substrate 66 through a bonding wire. The lead frame 72 is bonded to a land 82 of the flexible substrate 54 with a solder. In other words, the temperature-humidity detecting element 52 is bonded to the land 82 of the flexible substrate 54 with a solder. The semiconductor substrate 66 is electrically connected to the flexible substrate 54 through the bonding wire and the lead frame 72. That is, the temperature-humidity detecting element 52 is electrically and mechanically connected to the land 82 through the solder.

The molded resin 74 encapsulates a part of the semiconductor substrate 66, a part of the lead frame 72 and the bonding wire. In the semiconductor substrate 66, the temperature detecting portion 68 and the humidity detecting portion 70 are exposed from the molded resin 74. That is, the semiconductor substrate 66 is molded in the molded resin 74 in an exposed manner. Also, a connecting portion of the lead frame 72 to be connected to the flexible substrate 54 is exposed from the molded resin 74.

The moisture permeable filter 76 is fixed to the molded resin 74. The moisture permeable filter 76 is adhered to the molded resin 74, and forms an inner space 78 with the molded resin 74. The temperature detecting portion 68 and the humidity detecting portion 70 are exposed to the inner space 78.

The flexible substrate 54 has a base 80 and a land 82. The base 80 is made of an electrically insulating material. The flexible substrate 54 has a base film and a cover film, as the base 80. The base film and the cover film have flat plate shapes each having a thickness in the Z direction, at the mounting portion 62.

The land 82 is an electrode of the flexible substrate 54, and is made of a metal material. The land 82 is arranged at a part of the base film, and a remaining portion of the base film where the land 82 is not arranged is covered with the cover film. Thus, the land 82 exposes from the base 80. The land 82 is arranged at least adjacent to a surface 54a of the flexible substrate 54. In the present embodiment, the land 82 is arranged only on a side adjacent to the surface 54a.

The flexible substrate 54 has a non-illustrated wiring layer. The wiring layer is made of a metal material, similar to the land 82. The wiring layer is arranged on the base film at a position different from the land 82, and is electrically connected to the land 82. The wiring layer is covered with the cover film. In other words, the wiring layer is disposed between the base film and the cover film. The mounting portion 62 is formed with through holes 84 into which first insertion portions 120, which will be described hereinafter, are inserted and arranged. The through holes 84 penetrate through the mounting portion 62 in the Z direction.

The rigid member 56 is made of a material having a thermal conductivity and a rigidity higher than those of the base 80. The rigid member 56 is, for example, made of a resin material, a metal material, or a ceramic material. In the present embodiment, the rigid member 56 is made of a metal material, such as SUS, or aluminum. The rigid member 56 has a flat plate shape having a thickness in the Z direction.

The rigid member 56 is adhered to the rear surface 54b of the mounting portion 62. For example, the rigid member 56 and the flexible substrate 54 are fixed to each other through an adhesive material. As another example, the rigid member 56 and the flexible substrate 54 may be fixed to each other by a thermo-compression bonding.

The mounting portion 62 is formed with through holes 86 into which the first insertion portions 120, which will be described hereinafter, are inserted and arranged. The through holes 86 penetrate the rigid member 56 in the Z direction. The flexible member 58 is arranged on the rigid member 56 on a side opposite to the mounting portion 62.

The flexible member 58 is made of a material having a thermal conductivity and a flexibility higher than those of the base 80. The flexible member 58 is, for example, made of a silicone sheet in which the a filler is added. The flexible member 58 has a flat plate shape having a thickness in the Z direction.

The flexible member 58 is arranged in contact with the rigid member 56 and the attachment member 200, in between the rigid member 56 and the attachment member 200. Specifically, the flexible member 58 is adhered to the rigid member 56 and the attachment member 200. In the present embodiment, the rigid member 56 has a contact surface 56a to contact with the flexible member 58, and the contact surface 56a is a plane orthogonal to the Z direction.

The temperature-humidity detecting element 52 is arranged on the mounting portion 62 that is a part of the flexible substrate 54, the part overlapping with the rigid member 56 and the flexible member 58 when the flexible substrate 54 is projected in the Z direction. That is, the temperature-humidity detecting element 52 overlaps with the mounting portion 62, the rigid member 56 and the flexible member 58 in a projection view projected in the Z direction.

The housing 110 has the pressing portion 116 that presses the flexible substrate 54 toward the attachment member 200. The housing 110 corresponds to a pressing member. The pressing portion 116 includes pillar portions 118 extending from the flat plate portion 112 toward the attachment member 200, and the first insertion portions 120 that are inserted to and arranged in the through holes 84 and the through holes 86.

Each of the pillar portions 118 has a pillar shape having a longitudinal direction in the Z direction. In FIG. 3, the pillar portions 118 are illustrated with an alternate long and short dash line. As shown in FIG. 3, the planar shape of the pillar portion 118 is a substantially rectangular shape. The first insertion portion 120 projects from an end of the pillar portion 118 adjacent to the attachment member 200. The planar shape of the first insertion portion 120 is substantially the same as the planar shape of the through hole 84, and is substantially a circular shape.

The planar shape of the pillar portion 118 is greater than the planar shape of the first insertion portion 120. Thus, at the end of the pillar portion 118 adjacent to the attachment member 200, a portion where the first insertion portion 120 is not formed is in contact with the surface 54a. In the present embodiment, the number of the pillar portions 118 is two, and the number of the first insertion portions 120 is two.

In an assembling process, the first insertion portions 120 are inserted into the through holes 84 and the through holes 86, so the housing 110 is arranged to the flexible substrate 54 and the rigid member 56. Since the first insertion portions 120 are inserted into the through holes 84 and the through holes 86, the housing 110 can be easily positioned relative to the flexible substrate 54 and the rigid member 56. Further, since the first insertion portions 120 are inserted to and arranged in the through holes 84 and the through holes 86, the housing 110 is restricted from moving relative to the flexible substrate 54 and the rigid member 56 in a direction orthogonal to the Z direction.

Next, effects of the above-described sensor device 10 will be described.

In the present embodiment, the flexible member 58 is closely in contact with the attachment member 200 and the rigid member 56 by being pressed by the pressing portion 116. The rigid member 56 is adhered to the flexible substrate 54. As such, heat is easily conducted from the attachment member 200 to the temperature-humidity detecting element 52 through the flexible member 58, the rigid member 56 and the flexible substrate 54. In other words, thermal conduction from the attachment member 200 to the temperature-humidity detecting element 52 can be ensured.

In the present embodiment, since the flexible substrate 54 is adhered to the rigid member 56, the flexible substrate 54 is hardly deformed in the assembling process. Therefore, a degradation of reliability in electric connection between the flexible substrate 54 and the temperature-humidity detecting element 52 can be suppressed.

In the present embodiment, the LED 24, the PD 30, the arithmetic unit 32 and the PD 42 are mounted on the printed board 22, and the temperature-humidity detecting element 52 is mounted on the flexible substrate 54. Therefore, heat conduction from the electronic components mounted on the printed board 22 to the temperature-humidity detecting element 52 can be suppressed.

(Second Embodiment)

In the following description, portions of the present embodiment common to the sensor device 10 of the first embodiment will be omitted.

In the present embodiment, similar to the first embodiment, the rigid member 56 is made of a metal material. The rigid member 56 is electrically connected to the flexible substrate 54 at a non-illustrated position. For example, a through hole is formed in the mounting portion 62, so that a land 82 is exposed in a space surrounded by the through hole. A solder is applied to the through hole, so that the flexible substrate 54 and the rigid member 56 are electrically connected to each other.

Since the rigid member 56 is electrically connected to the flexible substrate 54, a potential of the rigid member 56 is fixed to a predetermined potential. As the predetermined potential, for example, a power source potential or a ground potential may be used.

Figure 4:
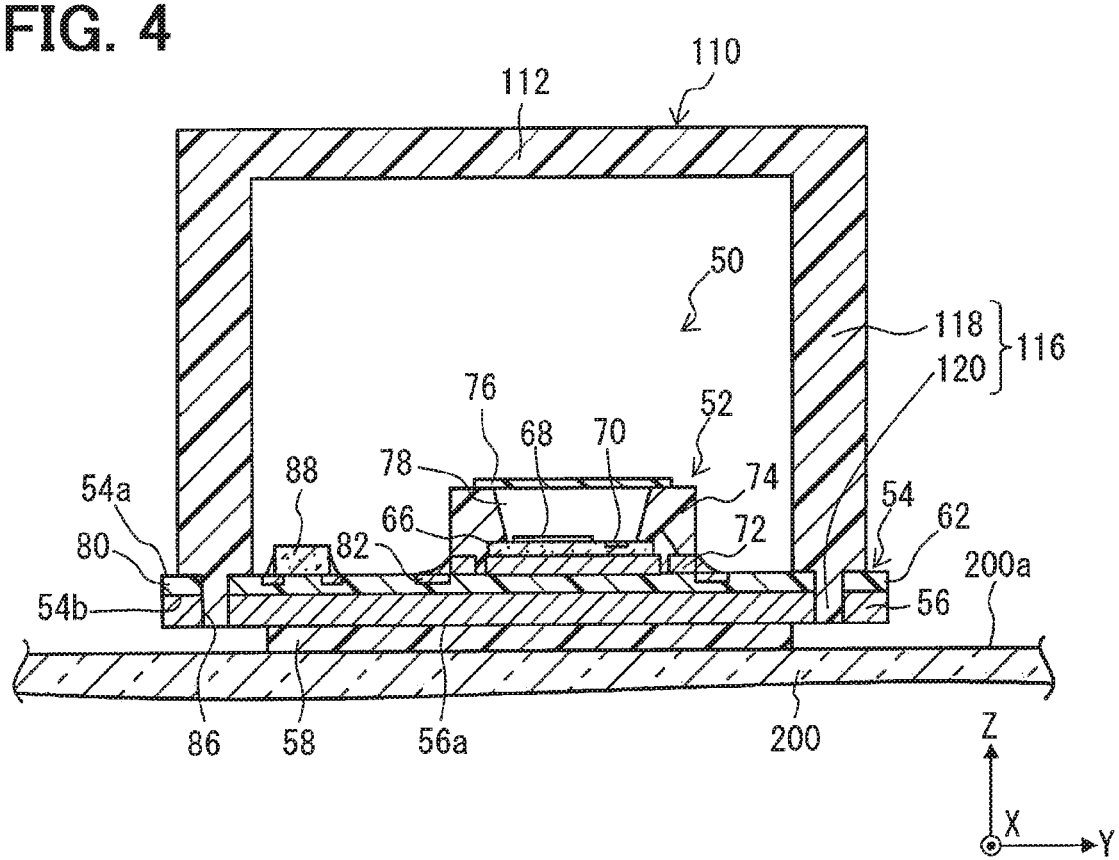
FIG. 4 is a cross-sectional view for illustrating a specific structure of a temperature-humidity detection unit of a sensor device according to a second embodiment.

In the present embodiment, as shown in FIG. 4, the temperature-humidity detection unit 50 includes a capacitor 88. The capacitor 88 restricts the potential of the rigid member 56 from varying. The capacitor 88 is electrically connected to the flexible substrate 54 and the rigid member 56. In the present embodiment, the capacitor 88 is a chip capacitor, and is mounted on the surface 54a.

In the structure where the rigid member 56 is made of the metal material, the flexible substrate 54 and the rigid member 56 are easily electrically connected to each other through a parasitic capacitance. If the flexible substrate 54 and the rigid member 56 are electrically connected to each other through the parasitic capacitance, there is a fear that the potential at a connecting portion of the flexible substrate 54 to the rigid member 56 varies.

In the present embodiment, on the other hand, it is possible to restrict the flexible substrate 54 and the rigid member 56 from being electrically connected to each other through a parasitic capacitance. Therefore, it is possible to restrict the potential of the connecting portion of the flexible substrate 54 to the rigid member 56 from being varied. In the present embodiment, further, the variation in potential of the flexible substrate 54 can be effectively suppressed by the capacitor 88.

(Third Embodiment)

In the following description of the present embodiment, explanations of portions common to the sensor device 10 of the first embodiment will be omitted.

Figure 5:
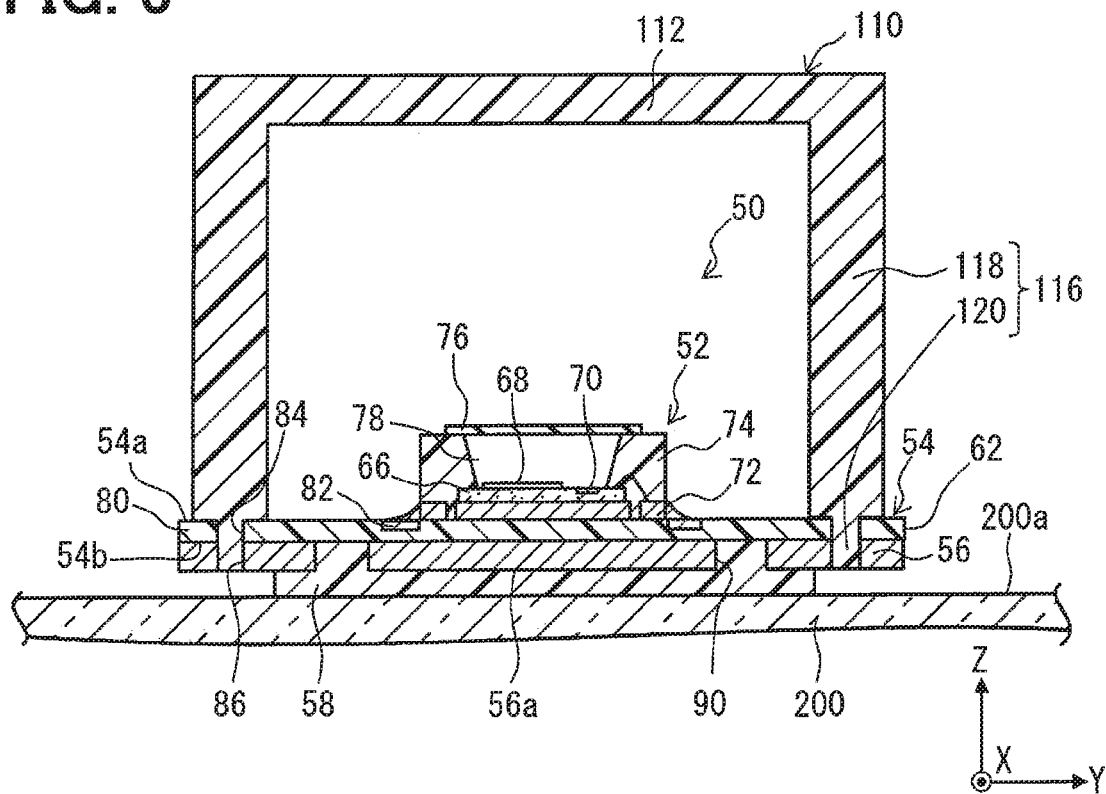
FIG. 5 is a cross-sectional view for illustrating a specific structure of a temperature-humidity detection unit of a sensor device according to a third embodiment.

As shown in FIG. 5, the rigid member 56 has through holes 90 extending in the Z direction. In the projection view projected in the Z direction, the through holes 90 are located at positions overlapping with the flexible member 58. In the XY plane, the through holes 90 are located at positions different from the through holes 86.

Portions of the flexible member 58 are located in the through holes 90. Specifically, in an assembling process, the flexible member 58 is deformed and is arranged in the through holes 90 as being pressed by the pressing portion 116.

In the present embodiment, the portions of the flexible member 58 arranged in the through holes 90 restrict the rigid member 56 from being moved in direction orthogonal to the Z direction. As such, it is possible to restrict the entirety of the rigid member 56 from being moved relative to the flexible member 58.

In the present embodiment, as compared with a structure in which the rigid member 56 is not formed with the through holes 90, a contact surface area between the flexible member 58 and the rigid member 56 can be increased. Therefore, heat can be effectively conducted from the flexible member 58 to the rigid member 56.

(Fourth Embodiment)

In the following description of the present embodiment, explanations of portions common to the sensor device 10 of the first embodiment will be omitted.

Figure 6:
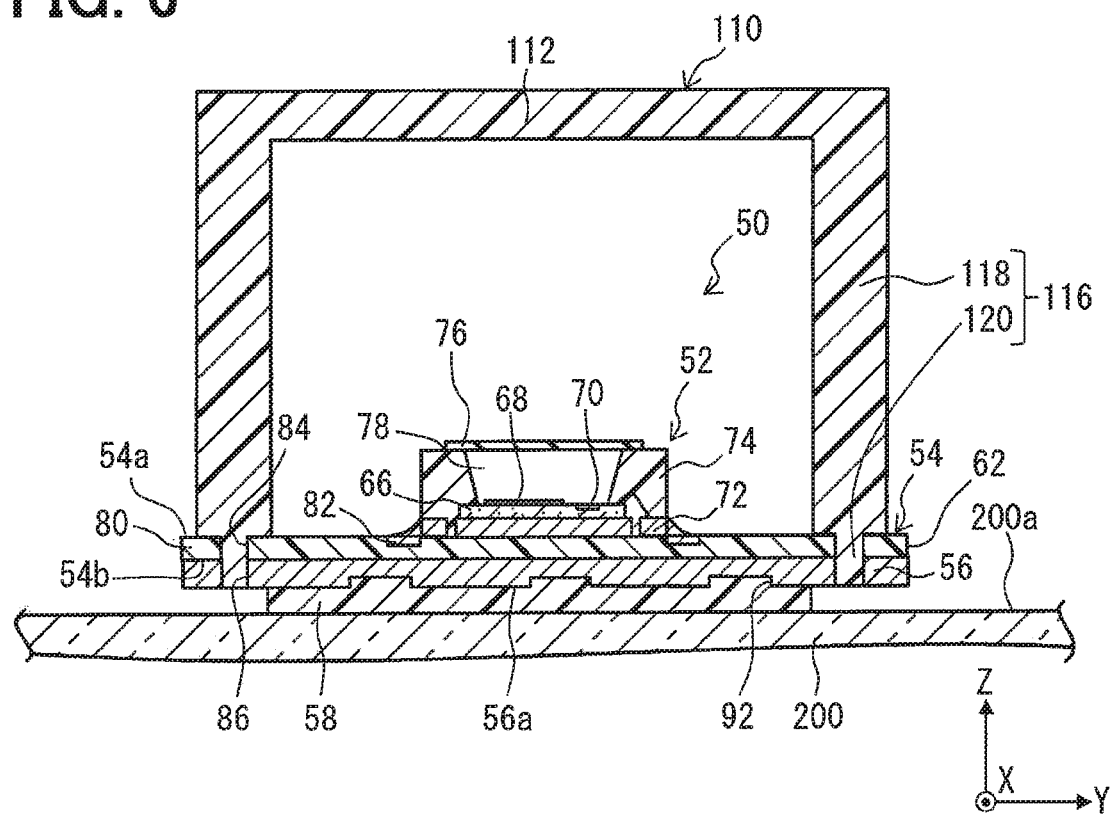
FIG. 6 is a cross-sectional view for illustrating a specific structure of a temperature-humidity detection unit of a sensor device according to a fourth embodiment.

As shown in FIG. 6, the contact surface 56a of the rigid member 56 has projections and recesses. In the present embodiment, the rigid member 56 is formed with a plurality of bottomed holes 92, and thus the contact surface 56a is a surface having projections and recesses. In the rigid member 56, the bottomed holes 92 are recessed in a direction separating from the attachment member 200. In the projection view projected in the Z direction, the bottomed holes 92 are located at positions overlapping with the flexible member 58. In the XY plane, the bottomed holes 92 are located at positions different from the through holes 86.

Portions of the flexible member 58 are arranged in the bottomed holes 92. Specifically, the flexible member 58 are deformed and are arranged in the bottomed holes 92 as being pressed by the pressing portion 116 in the assembling process.

In the present embodiment, a movement of the rigid member 56 relative to the flexible member 58 can be restricted, as compared with the structure in which the contact surface 56a is a flat surface. Also, a contact surface area between the flexible member 58 and the rigid member 56 can be increased, as compared with the structure in which the contact surface 56a is the flat surface. Accordingly, heat can be effectively conducted from the flexible member 58 to the rigid member 56.

(Fifth Embodiment)

In the following description of the present embodiment, explanations of portions common to the sensor device 10 of the first embodiment will be omitted.

Figure 7:
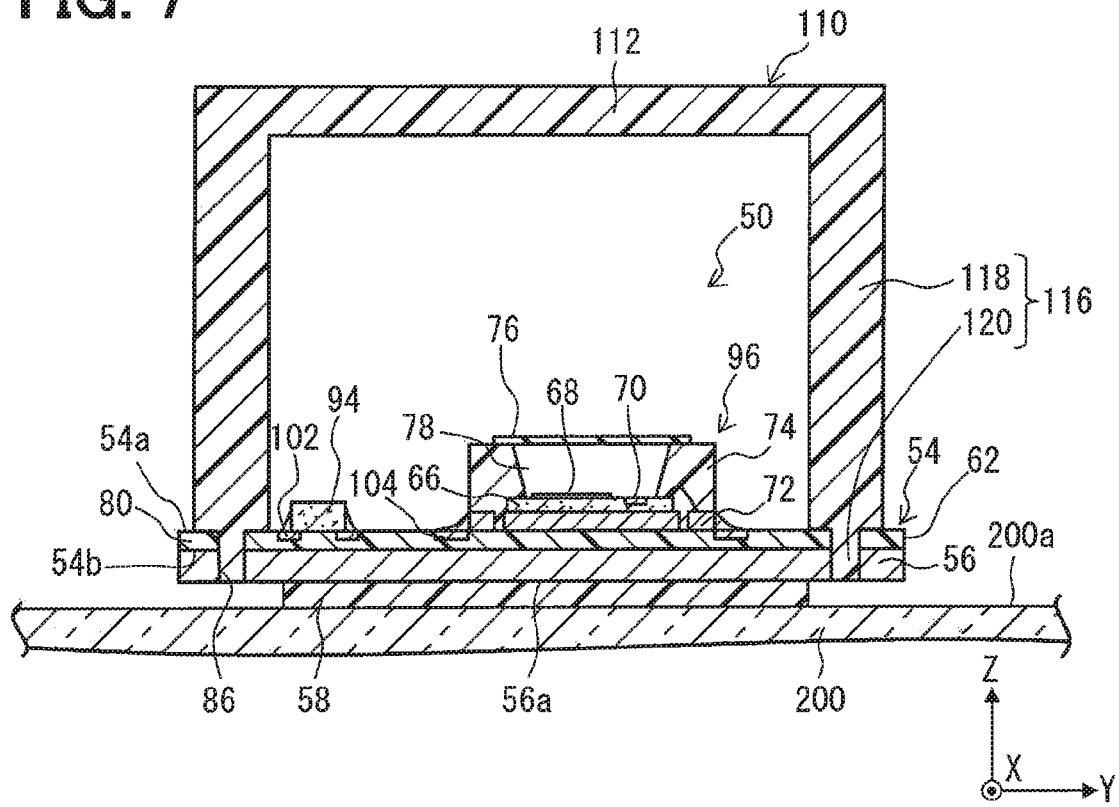
FIG. 7 is a cross-sectional view for illustrating a specific structure of a temperature-humidity detection unit of a sensor device according to a fifth embodiment.

As shown in FIG. 7, the temperature-humidity detection unit 50 includes a temperature detecting element 94 and a humidity detecting element 96. The temperature detecting element 94 detects the temperature of the attachment member 200. The humidity detecting element 96 detects a humidity in the vicinity of the surface 200a. The humidity detecting element 96 is provided separate from the temperature detecting element 94.

The flexible substrate 54 has a first land 102 electrically connected to the temperature detecting element 94, and a second land 104 electrically connected to the humidity detecting element 96. The first land 102 and the second land 104 are arranged on a side adjacent to the surface 54a. Thus, the temperature detecting element 94 and the humidity detecting element 96 are mounted on the surface 54a.

(Sixth Embodiment)

In the following description of the present embodiment, explanations of portions common to the sensor device 10 of the first embodiment will be omitted.

Figure 8:
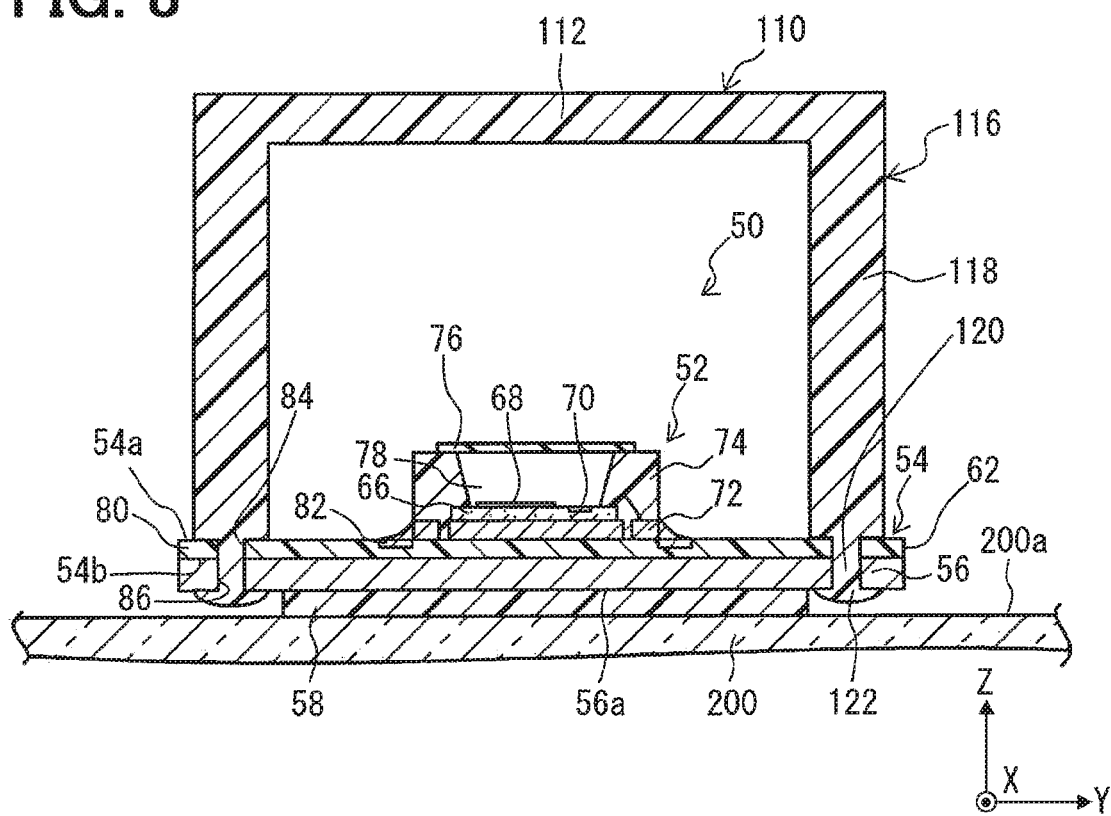
FIG. 8 is a cross-sectional view for illustrating a specific structure of a temperature-humidity detection unit of a sensor device according to a sixth embodiment.

As shown in FIG. 8, the pressing portion 116 is fixed to the flexible substrate 54 and the rigid member 56 by crimping. The pressing portion 116 has a first contact portion 122 that contacts with the contact surface 56a. The first contact portion 122 is disposed on a side of the first insertion portion 120 adjacent to the attachment member 200. A planar shape of the first contact portion 122 is greater than the planar shape of the through hole 86. The flexible substrate 54 and the rigid member 56 are held between the pillar portions 118 and the first contact portions 122 in the Z direction. The first contact portion 122 is, for example, formed by thermal deformation.

In the present embodiment, the housing 110 can be firmly fixed to the flexible substrate 54 and the rigid member 56. Therefore, movement of the housing 110 relative to the flexible substrate 54 and the rigid member 56 can be effectively restricted.

(Seventh Embodiment)

In the following description of the present embodiment, explanations of portions common to the sensor device 10 of the first embodiment will be omitted.

Figure 9:
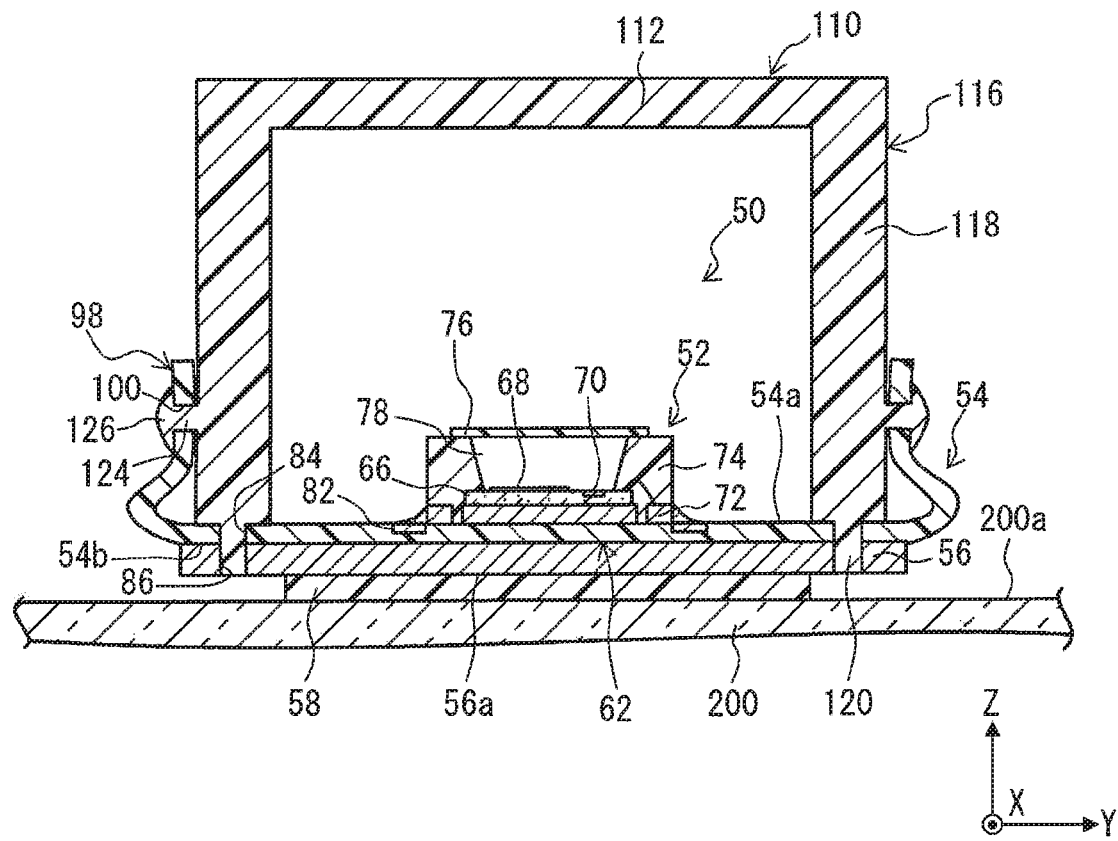
FIG. 9 is a cross-sectional view for illustrating a specific structure of a temperature-humidity detection unit of a sensor device according to a seventh embodiment.

As shown in FIG. 9, the housing 110 is fixed to the flexible substrate 54 at positions different from the first insertion portions 120. The flexible substrate 54 has extending portions 98 extending in the Z direction from ends of the mounting portion 62, the ends of the mounting portion 62 being opposite in the Y direction. The extending portions 98 extending in directions opposite to the attachment member 200. The extending portions 98 are opposed to the pillar portions 118 in the Y direction. The extending portions 98 have through holes 100 formed in the Y direction.

The pressing portion 116 has second insertion portions 124 and second contact portions 126. The second insertion portions 124 are inserted into and arranged in the through holes 100. The second contact portions 126 are in contact with surfaces of the extending portions 98 opposite to the pillar portions 118. The second insertion portions 124 project from the pillar portions 118 toward the extending portions 98 in the Y direction. The second contact portions 126 are located opposite to the pillar portions 118 with respect to the second insertion portions 124.

In an assembling process, the second contact portions 126 are inserted into the through holes 100 while deforming the extending portions 98, so the second insertion portions 124 pass through the through holes 100. In this method, it is not necessary to form the second contact portion 126 by crimping. In the present embodiment, therefore, the assembling process is simplified, and the housing 110 can be firmly fixed to the flexible substrate 54 and the rigid member 56.

(Eighth Embodiment)

In the following description of the present embodiment, explanations of portions common to the sensor device 10 of the first embodiment will be omitted.

Hereinafter, a surface of the flexible member 58 adjacent to the rigid member 56 will be referred to as the surface 58a, and a surface of the flexible member 58 opposite to the surface 58a will be referred to as the rear surface 58b. The surface 58a is a contact surface of the flexible member 58 that contacts with the rigid member 56. That is, the surface 58a is in contact with the contact surface 56a. The rear surface 58b is a surface that is in contact with the attachment member 200.

Figure 10:
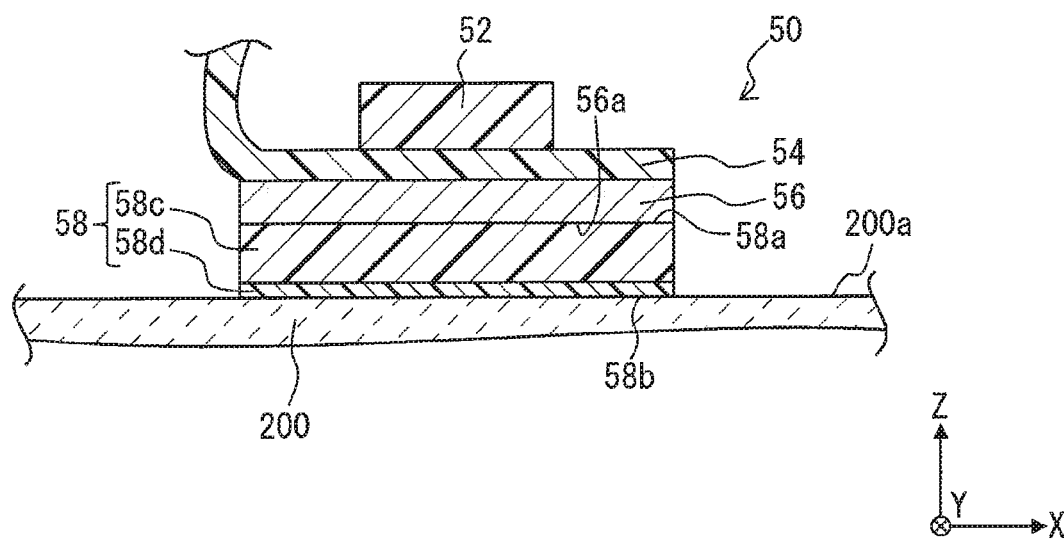
FIG. 10 is a cross-sectional view for illustrating a specific structure of a temperature-humidity detection unit of a sensor device according to an eighth embodiment.

As shown in FIG. 10, in the present embodiment, the flexible member 58 includes a silicone sheet 58c and a PET sheet 58d. PET is polyethylene terephthalate. As such, the flexible member 58 is made of two members each having a sheet shape. The silicone sheet 58c corresponds to a first sheet. The PET sheet 58d corresponds to a second sheet.

The silicone sheet 58c is adhered to the rigid member 56. Thus, a surface of the silicone sheet 58c adjacent to the rigid member 56 forms the surface 58a of the flexible member 58. The silicone sheet 58c has a thickness of approximately from 1.5 to 2.0 mm. The PET sheet 58d is adhered to the silicone sheet 58c on a side opposite to the rigid member 56. Thus, in the Z direction, the attachment member 200, the PET sheet 58d, the silicone sheet 58c and the rigid member 56 are laid on top of another in this order.

The PET sheet 58d is disposed between the silicone sheet 58c and the attachment member 200, and is in contact with both of the silicone sheet 58c and the attachment member 200. That is, the surface of the PET sheet 58d adjacent to the attachment member 200 provides the rear surface 58b of the flexible member 58. The thickness of the PET sheet 58d is smaller than that of the silicone sheet 58c, and is for example approximately from 10 μm to 20 μm. In the present embodiment, the thickness of the PET sheet 58d is approximately 12 μm.

The silicone sheet 58c has an adhesive property higher than that of the PET sheet 58d. In other words, the PET sheet 58d has an adhesive property lower than that of the silicone sheet 58c. As such, the surface 58a has an adhesive strength higher than that of the rear surface 58b. In other words, the rear surface 58b has an adhesive strength lower than that of the surface 58a. Namely, the flexible member has a difference in the adhesive strength between the surface 58a adjacent to the rigid member 56 and the rear surface 58b adjacent to the attachment member 200.

An adhesive strength between the silicone sheet 58c and the rigid member 56 is higher than an adhesive strength between the PET sheet 58d and the attachment member 200. In other words, the adhesive strength between the PET sheet 58d and the attachment member 200 is lower than the adhesive strength between the silicone sheet 58c and the rigid member 56. Further, an adhesive strength between the silicone sheet 58c and the PET sheet 58d is higher than the adhesive strength between the PET sheet 58d and the attachment member 200.

As a method for assembling the sensor device 10, the silicone sheet 58c is adhered to the rigid member 56, and the PET sheet 58d is adhered to the silicone sheet 58c. Further, the sensor device 10 is arranged on the attachment member 200 so that the PET sheet 58d is in contact with the surface 200a.

There is a case where the attachment member 200 will be replaced, for example, if the attachment member 200 is cracked. In such a case, the sensor device 10 is removed from the attachment member 200 before the attachment member 200 is replaced, and is then attached to new attachment member 200. That is, there is a case where the sensor device 10 is reused.

It is noted that the bracket is fixed to the attachment member 200 through an adhesive. Therefore, it is difficult to remove the bracket from the attachment member 200. In the case where the sensor device 10 is to be reused, new bracket will be used, without removing the bracket from the attachment member 200 that is to be replaced.

As a method for removing the sensor device 10 from the attachment member 200, a spring element is removed from the bracket. Thus, the portions of the sensor device 10 other than the bracket can be removed from the attachment member 200. In this case, if the adhesive strength between the flexible member 58 and the attachment member 200 is high, the flexible member 58 is difficult to be removed from the attachment member 200. In this case, therefore, new flexible member 58 is necessary, similar to the bracket, when the sensor device 10 is reused.

In the present embodiment, on the other hand, the adhesive strength of the rear surface 58b is lower than the adhesive strength of the surface 58a. Therefore, the adhesive strength between the PET sheet 58d and the attachment member 200 is lower than the adhesive strength between the silicone sheet 58c and the rigid member 56. As such, the flexible member 58 can be easily removed from the attachment member 200, when the sensor device 10 is removed from the attachment member 200. Therefore, when the sensor device 10 is removed to be reused, the flexible member 58 can be removed from the attachment member 200 and is then attached to the new attachment member 200. Accordingly, the costs for using new flexible member 58 can be suppressed.

In the present embodiment, the adhesive strength of the surface 58a is higher than the adhesive strength of the rear surface 58b. Therefore, the adhesive strength between the silicone sheet 58c and the rigid member 56 is higher than the adhesive strength between the PET sheet 58d and the attachment member 200. In the present embodiment, furthermore, the adhesive strength between the silicone sheet 58c and the PET sheet 58d is greater than the adhesive strength between the PET sheet 58d and the attachment member 200.

In this case, when the sensor device 10 is removed from the attachment member 200, the silicone sheet 58c is hardly separated from the rigid member 56 as well as the PET sheet 58d is hardly separated from the silicone sheet 58c. That is, the flexible member 58 is hardly separated from the rigid member 56. Therefore, when the sensor device 10 is attached to new attachment member 200, it is not necessary to newly adhere the flexible member 58 to the rigid member 56. That is, when the sensor device 10 is reused, the process of attaching the sensor device 10 to the attachment member 200 can be simplified.

Figure 11:
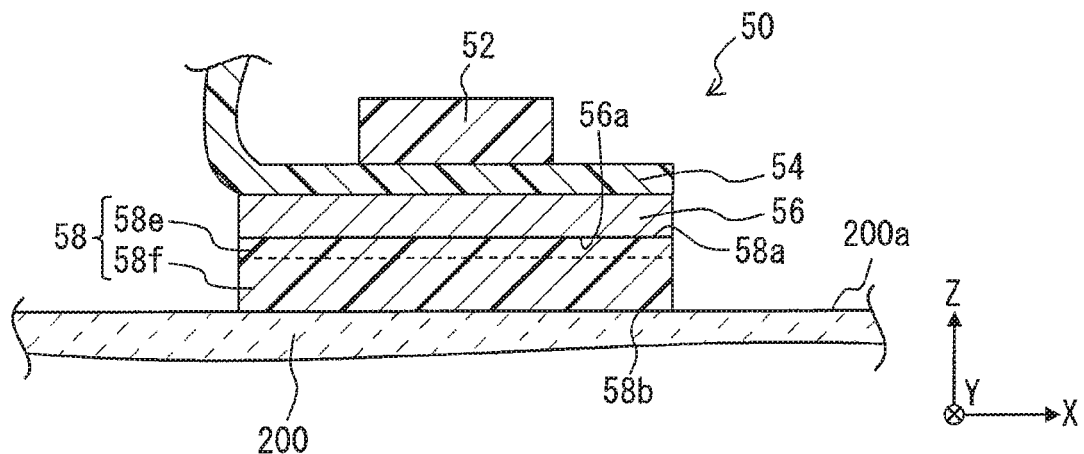
FIG. 11 is a cross-sectional view for illustrating a specific structure of a temperature-humidity detection unit of a sensor device according to a first modification.

In the present embodiment, the flexible member 58 exemplarily has the silicone sheet 58c and the PET sheet 58d. However, the flexible member 58 is not limited to the example described in the present embodiment. As shown in a first modification of FIG. 11, a silicone sheet including a first layer 58e with an excellent adhesive property and a second layer 58f with an adhesive property lower than the first layer 58e may be employed as the flexible member 58. Note that, in FIG. 11, a boundary between the first layer 58e and the second layer 58f is illustrated with a dashed line for the purpose of convenience.

The first layer 58e is adhered to the rigid member 56. That is, the surface of the first layer 58e adjacent to the rigid member 56 provides the surface 58a of the flexible member 58. The second layer 58f is provided on the first layer 58e on a side opposite to the rigid member 56. The second layer 58f is in contact with the attachment member 200. That is, a surface of the second layer 58f adjacent to the attachment member 200 provides the rear surface 58b of the flexible member 58.

The first layer 58e is formed by irradiating the surface 58a of the silicone sheet with ultraviolet (UV). That is, the first layer 58e is formed by performing UV treatment to the silicone sheet.

The first layer 58e which has been subjected to the UV treatment has an adhesive property higher than the second layer 58f that is not subjected to the UV treatment. Thus, the surface 58a has an adhesive strength higher than the rear surface 58b. The adhesive strength between the first layer 58e and the rigid member 56 is higher than the adhesive strength between the second layer 58f and the attachment member 200. In other words, the adhesive strength between the second layer 58f and the attachment member 200 is lower than the adhesive strength between the first layer 58e and the rigid member 56.

Figure 12:
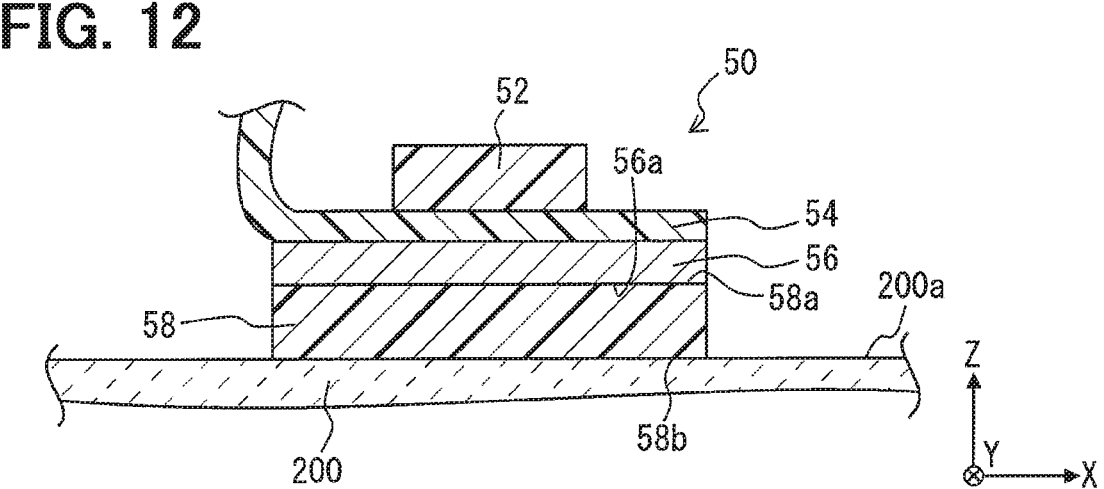
FIG. 12 is a cross-sectional view for illustrating a specific structure of a temperature-humidity detection unit of a sensor device according to a second modification.

As shown in a second modification of FIG. 12, the flexible member 58 may be formed by potting a liquid resin to the rigid member 56. After potting onto the rigid member 56, the resin is cured such as by heating. In this way, the flexible member 58 can be formed. After the flexible member 58 is formed by curing the resin, the sensor device 10 is arranged on the attachment member 200 so that the rear surface 58b of the flexible member 58 is in contact with the surface 200a.

In this example, since the resin is in a liquid state during the potting, the resin enters fine asperities on the contact surface 56a Therefore, as compared with the method in which a silicone sheet is arranged on the rigid member 56, a contact surface between the flexible member 58 and the rigid member 56 is increased. The number of atomic bonding of the resin potted reduces when the resin cured. Therefore, although the number of atomic bonding of the resin that contacts with the rigid member 56 is large during the potting, the number of atomic bonding of the flexible member 58 contacting with the attachment member 200 is small when the sensor device 10 is arranged on the attachment member 200. As such, the rear surface 58b has the adhesive strength lower than the surface 58a.

Figure 13:
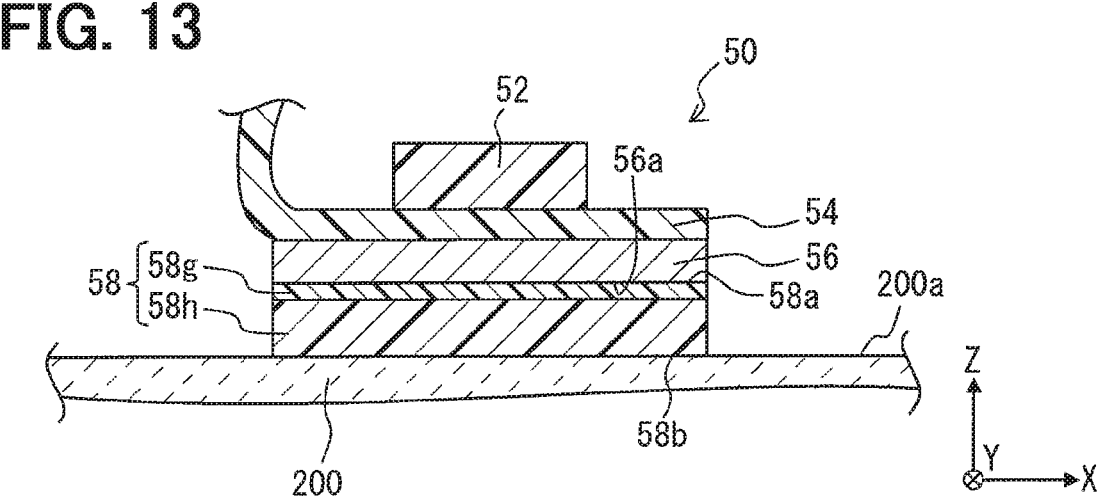
FIG. 13 is a cross-sectional view for illustrating a specific structure of a temperature-humidity detection unit of a sensor device according to a third modification.

As shown in a third modification in FIG. 13, the flexible member 58 may be provided by a primer 58g and a silicone sheet 58h. The primer 58g is a tackiness agent. Alternatively, the primer 58g can be an adhesive.

The primer 58g is applied to the silicone sheet 58h to adhere the silicone sheet 58h to the rigid member 56. That is, the primer 58g is adhered to both of the rigid member 56 and the silicone sheet 58h. A surface of the primer 58g adjacent to the rigid member 56 corresponds to the surface 58a of the flexible member 58.

A surface of the silicone sheet 58h opposite to the primer 58g is in contact with the attachment member 200. That is, the surface of the silicone sheet 58h adjacent to the attachment member 200 provides the rear surface 58b of the flexible member 58.

The adhesive strength between the primer 58g and the rigid member 56 is higher than the adhesive strength between the silicone sheet 58h and the attachment member 200. In other words, the adhesive strength between the silicone sheet 58h and the attachment member 200 is lower than the adhesive strength between the primer 58g and the rigid member 56. Further, the adhesive strength between the primer 58g and the silicone sheet 58h is higher than the adhesive strength between the silicone sheet 58h and the attachment member 200.

In the third modification, similar to the eighth embodiment, a PET sheet may be provided between the silicone sheet 58h and the attachment member 200. That is, the flexible member 58 may have the PET sheet, in addition to the primer 58g and the silicone sheet 58h. In the third modification, similar to the first modification, the silicone sheet 58h may be subjected to the UV treatment from the rear surface 58b.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

In the embodiments described hereinabove, although the temperature-humidity detecting element 52 is exemplarily bonded to the flexible substrate 54 with a solder, it is just an example. The temperature-humidity detecting element 52 may be electrically connected to the flexible substrate 54 with a bonding wire and a silver paste.

In the embodiments described hereinabove, the sensor device 10 exemplarily includes the rain detection unit 20, the light detection unit 40, the temperature-humidity detection unit 50, the housing 110 and the connector 130. However, the sensor device 10 will not be limited to such an example. The sensor device 10 may have any structure as long as the sensor device 10 is attached to the attachment member 200 and detects the temperature of the attachment member 200.

In the embodiments described hereinabove, the temperature-humidity detecting element 52 exemplarily has the semiconductor substrate 66, the lead frame 72, the molded resin 74, and the moisture permeable filter 76. However, the temperature-humidity detecting element 52 will not be limited to one having such components. The temperature-humidity detecting element 52 may not have the lead frame 72 and the molded resin 74. Also, the semiconductor substrate 66 may be accommodated in a ceramic case or a resin case.

In the embodiments described hereinabove, the pressing portion 116 exemplarily have the pillar portions 118 and the first insertion portions 120. However, the structure of the pressing portion 116 will not be limited to such structures. In addition, the number of the pillar portions 118 and the number of the first insertion portions 120 are exemplarily two, respectively. However, the number of the pillar portions 118 and the number of the first insertion portions 120 will not be limited to two. Further, the planar shape of the pillar portions 118 is exemplarily substantially rectangle, and the planar shape of the first insertion portions 120 is exemplarily substantially circle. However, the planar shapes of the pillar portions 118 and the first insertion portions 120 will not be limited to these examples.

The invention claimed is:

1. A sensor device for detecting a temperature of an attachment member in an attached state in which the sensor device is attached to the attachment member, the sensor device comprising:
    a sensor element that detects the temperature of the attachment member;
    a flexible substrate that includes a base having a first surface and a second surface opposite to the first surface and being made of an electrically insulating material, and a land disposed adjacent to the first surface and electrically connected to the sensor element;
    a rigid member that has a thermal conductivity and a rigidity higher than those of the base, and is adhered to the second surface;
    a flexible member that has a thermal conductivity and a flexibility higher than those of the base, is stacked on the rigid member to be in contact with the rigid member on a side opposite to the flexible substrate, and is disposed to be in contact with the attachment member in the attached state; and
    a pressing member that presses the flexible substrate toward the attachment member in the attached state.

2. The sensor device according to claim 1, wherein the sensor element detects a humidity in a vicinity of the attachment member.

3. The sensor device according to claim 1, wherein the land is a first land, and
    the flexible substrate further includes a second land disposed adjacent to the first surface,
    the sensor device further comprising:
    a humidity detecting element that is electrically connected to the second land and detects a humidity in a vicinity of the attachment member.

4. The sensor device according to claim 1, wherein the rigid member is made of a metal material, and
    the rigid member is electrically connected to the flexible substrate and is fixed to a predetermined potential.

5. The sensor device according to claim 4, further comprising:
    a capacitor that restricts the potential of the rigid member from being varied, and is electrically connected to the flexible substrate and the rigid member.

6. The sensor device according claim 1, wherein
    the rigid member has a through hole that extends in a stacked direction of the rigid member and the flexible member, and is located at a position corresponding to the flexible member in a view projected in the stacking direction, and
    a part of the flexible member is disposed in the through hole in the attached state.

7. The sensor device according to claim 1, wherein
    the rigid member has a contact surface that contacts with the flexible member, and
    the contact surface has projections and recesses.

8. The sensor device according to claim 1, wherein
    the flexible member has a surface that contacts with the attachment member in the attached state, and
    the surface of the flexible member that contacts with the attachment member in the attached state has an adhesive strength lower than an adhesive strength of a surface of the flexible member that contacts with the rigid member.

9. The sensor device according to claim 8, wherein
    the flexible member has a first sheet that is adhered to the rigid member, and a second sheet that is adhered to the first sheet on a side opposite to the flexible member and is in contact with the attachment member in the attached state, and
    the first sheet has an adhesive property higher than the second sheet.

10. The sensor device according to claim 1, further comprising:
    a printed board that has a rigidity higher than the flexible substrate, and is electrically connected to the flexible substrate; and
    an electronic component provided to the printed board.

11. The sensor device according to claim 10, wherein
    the pressing member is a housing that accommodates the printed board therein, and is fixed to the attachment member in the attached state.

12. The sensor device according to claim 1, wherein the attachment member is a windshield of a vehicle.

13. The sensor device according to claim 1, wherein the sensor element is connected to the land through a solder.

\* \* \* \* \*